United States Patent [19]
Klein et al.

[11] Patent Number: 5,658,248
[45] Date of Patent: Aug. 19, 1997

[54] DOUBLE-BLIND INFUSION DEVICE AND METHOD

[75] Inventors: Enrique J. Klein; Aaron V. Kaplan, both of Los Altos, Calif.

[73] Assignee: LocalMed, Inc., Palo Alto, Calif.

[21] Appl. No.: 511,567

[22] Filed: Aug. 4, 1995

[51] Int. Cl.$^6$ .................................................. A61M 1/00
[52] U.S. Cl. .................................................. 604/32
[58] Field of Search ........................ 604/49, 32, 246, 604/248, 30, 31, 33, 34

[56] References Cited

U.S. PATENT DOCUMENTS

| | | |
|---|---|---|
| 857,739 | 6/1907 | Kennerly et al. |
| 1,215,512 | 2/1917 | Fetzer .................. 604/248 |
| 1,930,929 | 10/1933 | Eisenberg . |
| 2,261,213 | 11/1941 | Bierman .................. 604/248 |
| 2,421,959 | 6/1947 | Norris . |
| 2,485,842 | 10/1949 | Pennington .................. 604/248 |
| 2,842,124 | 7/1958 | James .................. 604/248 |
| 2,854,027 | 9/1958 | Kaiser et al. .................. 604/248 |
| 3,834,372 | 9/1974 | Turney .................. 604/248 |
| 3,952,919 | 4/1976 | Hansen et al. . |
| 3,957,082 | 5/1976 | Fuson et al. .................. 604/248 |
| 4,219,021 | 8/1980 | Fink .................. 604/248 |
| 4,253,501 | 3/1981 | Ogle .................. 604/246 |
| 4,256,111 | 3/1981 | Lassen . |
| 4,509,861 | 4/1985 | Sjonell . |
| 4,593,717 | 6/1986 | Levasseur .................. 604/248 |
| 4,604,093 | 8/1986 | Brown et al. .................. 604/248 |
| 4,634,027 | 1/1987 | Kanarvogel . |
| 4,758,235 | 7/1988 | Tu .................. 604/248 |
| 4,900,322 | 2/1990 | Adams .................. 604/248 |
| 4,904,243 | 2/1990 | Bruera . |
| 4,941,883 | 7/1990 | Venturini . |
| 5,135,026 | 8/1992 | Manska .................. 604/248 |
| 5,439,452 | 8/1995 | McCarty .................. 604/248 |
| 5,443,453 | 8/1995 | Walker et al. .................. 604/248 |
| 5,466,228 | 11/1995 | Evans .................. 604/248 |
| 5,468,230 | 11/1995 | Corn .................. 604/248 |

*Primary Examiner*—Robert A. Hafer
*Assistant Examiner*—Manuel Mendez
*Attorney, Agent, or Firm*—Townsend and Townsend and Crew LLP

[57] ABSTRACT

Type-A (operational) and type-B (non-operational) syringes (2A, 2B), used for double-blind clinical tests, are constructed so the type-B syringe mimics the operation of the type-A syringe while avoiding the delivery of anything into the patient. Each syringe includes an injector (4), a fluid connector (12) coupling the exit port (10) of the injector to a discharge port (14) to which a catheter or needle cannula is connected, a valve (18) positioned along the fluid connector, and a dumping reservoir (24) mounted to the valve. The type-A valve fluidly couples the exit port to the discharge port in both purging and infusion positions. The type-B valve couples the exit port to the discharge port in the purging position, but couples the exit port to the dumping reservoir in the infusion position. The infusate is directed through the catheter and into the patient when in the infusion position with the type-A valve but is directed into the dumping reservoir with the type-B valve.

18 Claims, 3 Drawing Sheets

DOUBLE-BLIND INFUSION DEVICE AND METHOD

BACKGROUND OF THE INVENTION

Double-blind studies are commonly conducted to determine the efficacy of a new drug therapy. In double-blinded studies neither the physician nor the patient know if the active agent or its placebo had been administered. This is done to insure objectivity when evaluating study end-points. With oral and intravenous medications it is relatively simple to prepare active agent (vehicle and agent) and the appropriate placebo control (containing vehicle only, without active agent). When studying site specific therapies, which is typically accomplished using an infusion catheter, there is concern regarding the active delivery of placebo to the site.

SUMMARY OF THE INVENTION

The present invention is directed to an infusion device especially adapted for use in double-blind clinical studies so that neither the patient nor the physician is provided with any indication as to whether an infusate is being delivered into the patient.

The infusion device can alternatively be a type-A (or operational) infusion device or a type-B (or non-operational) infusion device. While both types A and B are externally identical, the type-B infusion device mimics the operation of the type-A infusion device while avoiding the delivery of anything into the patient. Each of the type-A and type-B infusion devices include a infusion device element or other injector and a fluid connector coupling the exit port of the injector to a discharge port. A catheter or a hollow needle is typically connected to the discharge port. The infusion device also includes a valve positioned along the fluid connector and a dumping reservoir fluidly coupled to, and preferably mounted to, the valve.

The valve for the type-A infusion device is a type-A (or operational) valve which fluidly couples the exit port to the discharge port when in a purging position and when in an infusion position. The type-B infusion device includes a type-B (or non-operational) valve which couples the exit port to the discharge port when in the purging position, but isolates the exit port from the discharge port when in the infusion position; when in the infusion position, the type-B valve couples the exit port to the dumping reservoir. In this way, the infusate within the injector of a type-A syringe is directed into the patient through the catheter when in the infusion position; the infusate within the injection of a type-B valve is directed into the dumping reservoir when in the infusion position. The dumping reservoir is constructed so that the type-B infusion device mimics the operation of the type-A infusion device including the creation of a hydraulic back pressure to the movement of the infusate from the injector. The dumping reservoir preferably includes an anti-sloshing element, such as an absorbent material, to help mask the presence of the infusate within the dumping reservoir.

Other features and advantages of the invention will appear from the following description in which the preferred embodiment has been set forth in detail in conjunction with the accompanying drawings.

DESCRIPTION OF THE PREFERRED EMBODIMENT AND METHOD

Figure 1:
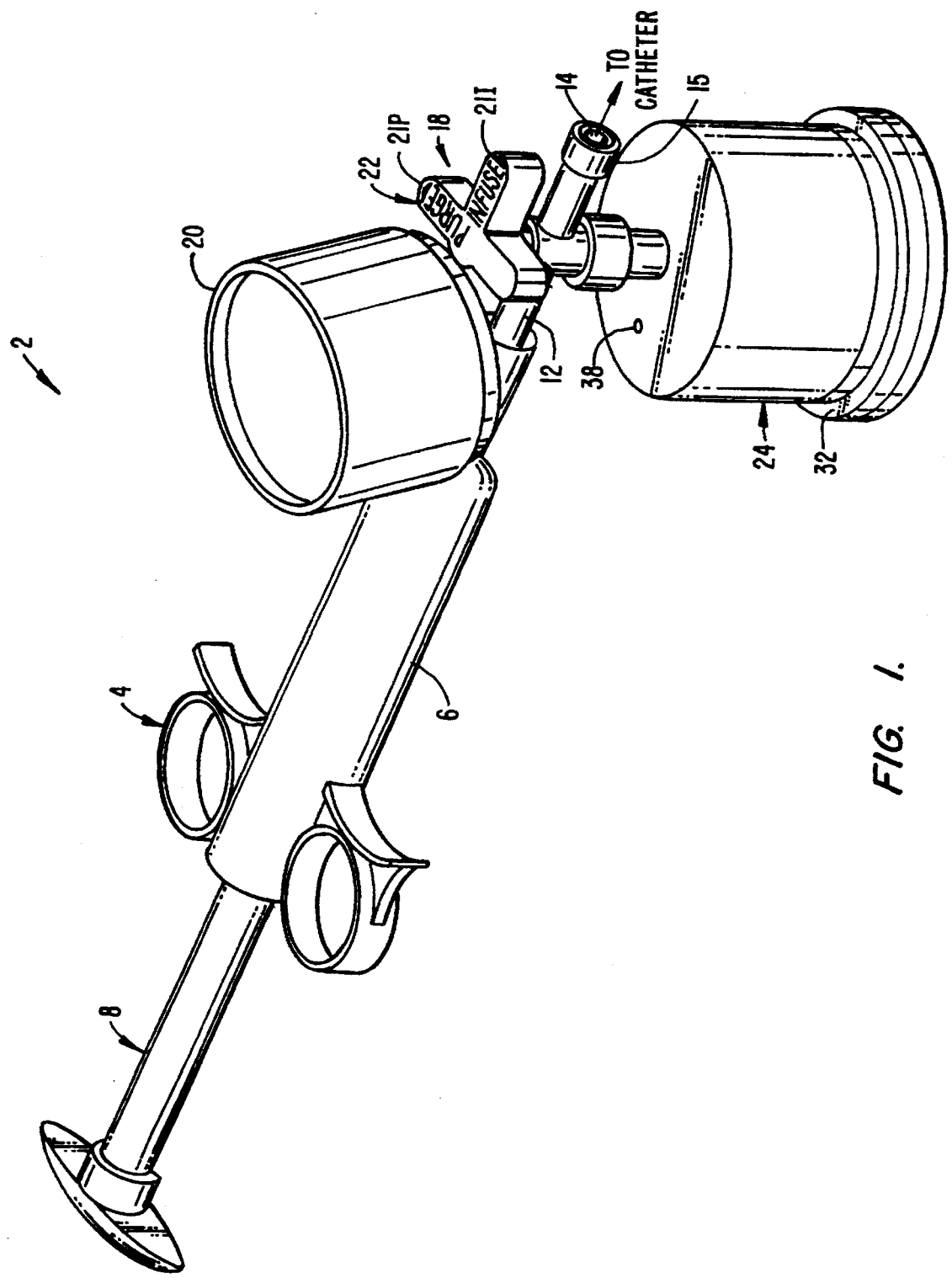
FIG. 1 is an overall view of an infusion device made according to the invention.
Figure 2:
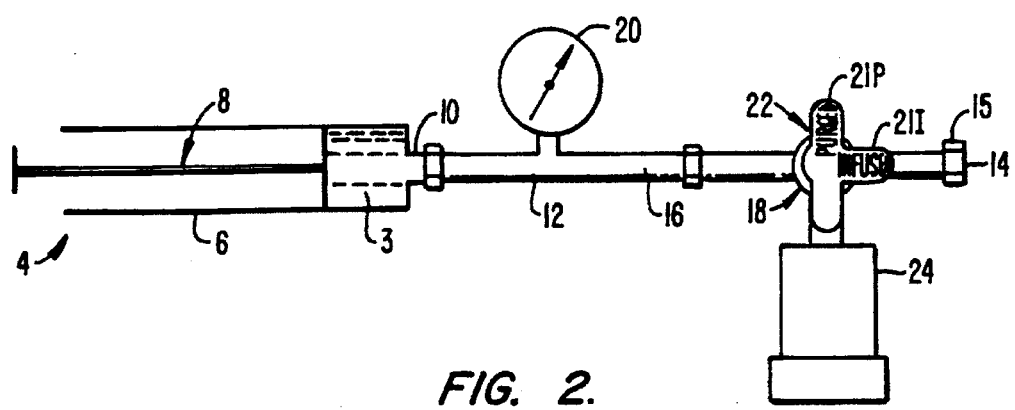
FIG. 2 is a simplified schematic representation of the components of the infusion device of FIG. 1.

FIGS. 1 and 2 illustrate an infusion syringe 2 suitable for use in double-blind clinical studies for delivering a liquid infusate 3 into a patient. Infusion syringe 2 includes a syringe element or injector 4 having a barrel 6 and a plunger 8. Barrel 6 has an exit port 10 to which a fluid connector 12 is mounted, preferably through a Luer fitting or other suitable attachment. Fluid connector 12 has a discharge port 14 at its distal end and at which a suitable catheter fitting 15 is positioned for mounting infusion syringe 2 to a catheter (not shown). Fluid connector 12 defines a fluid passageway 16 between exit port 10 and discharge port 14.

Fluid passageway 16 is interrupted by a valve 18. Valve 18 is of two types, a type-A (operational) valve and a type-B (non-operational) valve to create type-A (operational) and type-B (non-operational) infusion syringes 2. This will be discussed in more detail below. A pressure gauge 20 is also mounted along fluid connector 12 between valve 18 and exit port 10. Pressure gauge 20 is used to permit the physician administering infusate 3 to the patient to monitor the pressure the infusate is being delivered at, similarly to how a pressure gauge is used to monitor the inflation pressure of a balloon in angioplasty procedures.

Figure 3A:
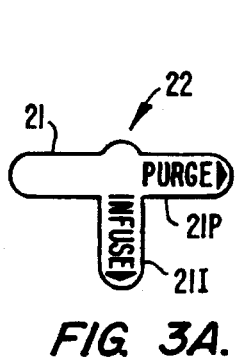
FIGS. 3A, 4A and 5A are top views of the valve handle of a type-A valve in purge, intermediate and infuse positions.
Figure 3B:
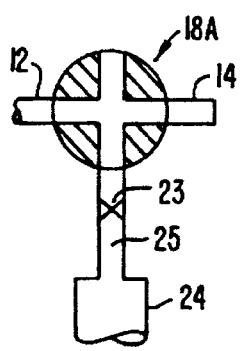
FIGS. 3B, 4B and 5B are simplified schematic views showing a type-A valve in purging, intermediate and infusion positions.
Figure 4A:
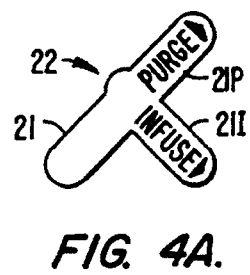
Figure 4B:
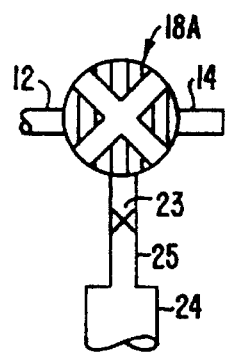
Figure 5A:
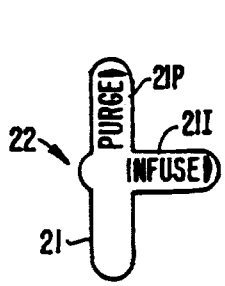
Figure 5B:
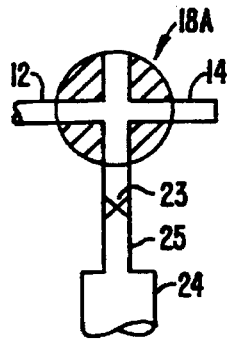

An operational valve 18A, see FIGS. 3B, 4B and 5B, is a modified three-way valve having four interconnected side branches movable among infusion, intermediate and purging positions. This valve is rotationally positionable. FIGS. 3A, 4A and 5A illustrate handle 22 of valve 18A in purge, intermediate and infuse positions corresponding to the same positions of FIGS. 3B, 4B and 5B. Handle 22 and the body of valve 18A are integrally built or fixedly connected to each other so as to always move (rotate) in unison. Handle 22 can have three arms 21, two of which are identified as arms 21P and 21I and are labeled with the words "PURGE" and "INFUSE" respectively. As suggested by FIGS. 3A and 3B, aligning purge arm 21P with discharge port 14 places valve 14A in the purge position, which can also be used to fill the syringe. Rotating handle 22 ⅛ turn counterclockwise, see FIG. 4A, moves valve 14A ⅛ turn counterclockwise to the intermediate position of FIG. 4B. As is discussed below, the intermediate position of valve 18A seals exit port 10 to allow the transfer or storage of the filled syringe, and to permit mounting and dismounting of, for example, a catheter or a needle cannula (not shown) to and from fitting 15. Valve 18A is then rotated ⅛ turn clockwise back to the purge position of FIG. 3B. Plunger 8 is then actuated to purge the infusion syringe and catheter of air.

After purging of the infusion syringe and catheter, valve 18A is placed in the intermediate position (FIG. 4B) once again and the catheter is introduced into the patient. Movement of handle 22 ⅛ turn counterclockwise to the infuse position of FIG. 5A causes valve 18A to move to the infuse position of FIG. 5B. With the type-A valve 18A, the infusion position of FIG. 5B permits the contents of injector 4 to be injected through connector 12, past discharge port 14, through the catheter and into the patient.

A dumping reservoir 24 is mounted to valve 18, but with operational syringe 2A, it is a dummy reservoir. That is, the fluid connection between valve 18A and the interior of dumping reservoir 24 is blocked regardless of the position of valve 18A. This is suggested in FIGS. 3B, 4B and 5B by a blockage 23 along the passageway 25 connecting valve 18A and dumping reservoir 24.

Figure 6A:
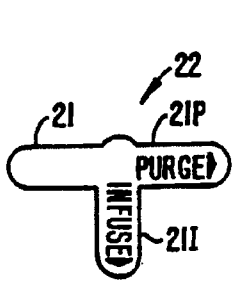
FIGS. 6A, 7A and 8A are top views of the valve handle of a type-B valve in the purging, intermediate and infusing/dumping positions.
Figure 6B:
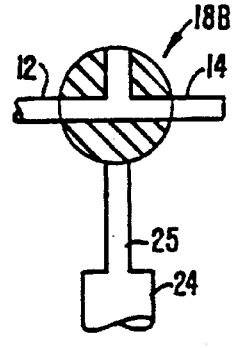
FIGS. 6B, 7B and 8B are simplified schematic views of a type-B valve shown in the purging, intermediate and infusing/dumping positions.
Figure 7A:
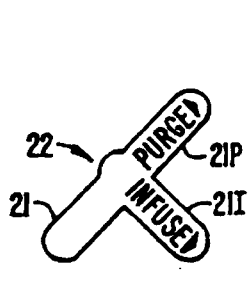
Figure 7B:
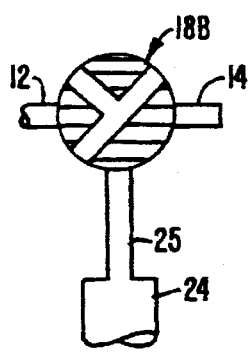
Figure 8A:
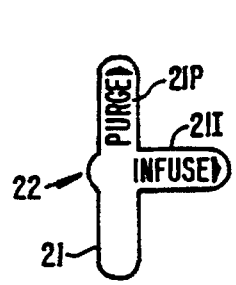
Figure 8B:
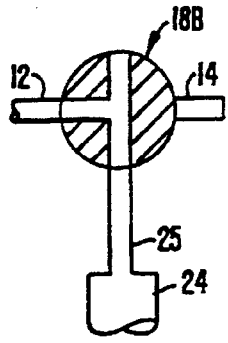

Valve 18B is a conventional three-way valve having three interconnected side branches as shown in FIGS. 6A, 7B and 8B. As with valve 18A, handle 22 and the body of valve 18B are integrally built or fixedly connected to each other so as to always move (rotate) in unison. FIGS. 6A and 6B show handle 22 and valve 18B in their purging positions, which, like with valve 18A, permits the user to purge the syringe 2 of air prior to connecting discharge port 14 to a catheter. After purging the air, handle 22 is rotated to the intermediate position of FIG. 7A to place valve 18B in the intermediate position of FIG. 7B. In this position of FIG. 7B, fluid passageway 16 upstream of valve 18 is sealed, thus sealing exit port 10, to permit the fluid-filled discharge port 14 to be mounted to the catheter. Valve 18B is then rotated ⅛ turn clockwise back to the purge position of FIG. 6B.

Figure 9:
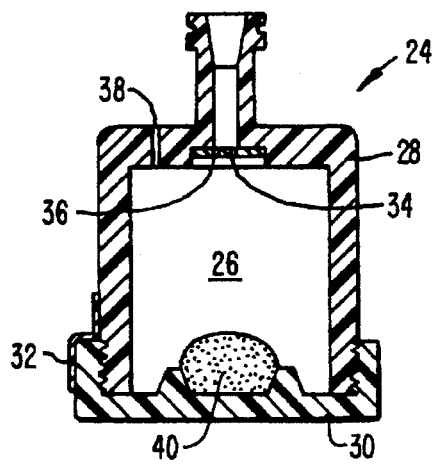
FIG. 9 is a cross-sectional view of the dumping reservoir of FIGS. 1 and 2.

Plunger 8 is then actuated to purge the catheter of air. After purging of the catheter, valve 18B is placed in the intermediate position (FIG. 7B) and the catheter is introduced into the patient. Valve 18B is then rotated ⅛ turn counterclockwise to the infusion position of FIG. 8B. With type-B valve 18B, the infusion position of FIGS. 8A and 8B causes discharge port 14 to be fluidly disconnected from exit port 10. Rather, exit port 10 is fluidly coupled to the interior 26 of dumping reservoir 24. See FIG. 9.

Dumping reservoir 24 includes a reservoir body 28 having, in this embodiment, a screw-on cap 30 at one end. Screw-on cap 30 is provided with a tamper-evident seal 32 to ensure that only investigators not blinded to the use of a particular device of type-A or type-B will be allowed to access to the contents of reservoir 24. The use and operation of non-operational infusion syringe 2B should fully mimic the use and operation of operational infusion syringe 2A.

To help provide this operational mimicry, dumping reservoir 24 has a restrictor plate 34 having one or more small orifices 36 to restrict passage of infusate 3 flowing into interior 26 of reservoir 24. At a predetermined pressure, as indicated by pressure gauge 20, it is desirable to attain an approximately equivalent fluid flow rate, and therefore plunger 8 velocity, when delivering the placebo into dumping reservoir 24. Thus, at a given flow rate, the pressure drop of the placebo passing through fluid connector 12, valve 18 and through restrictor plate 34, should correspond to the pressure drop of infusate 3 passing through fluid connector 12, valve 18, through the catheter and into the body.

A vent hole 38 is formed in body 28 to provide relief for the air within interior 26 as the air is being displaced by the fluid. Vent hole 38 is large enough to permit passage of air from interior 26 but small enough so that liquid does not leak out of interior 26. The exit vent hole 38 is preferably located in an unobtrusive location, or shielded from direct observation, to prevent the user or patient from noticing the presence of a fluid meniscus or a fluid leak on the surface of body 28 as an indication that syringe 2 is a non-operational syringe 2B. The operator will follow the same sequence of ⅛ turns each time but achieve different results with operational syringe 2A or non-operational syringe 2B.

Another way to ensure that no fluid appears at the exit vent hole 38, as well as keeping the liquid from sloshing around within interior 26 of dumping reservoir 24 of the type-B syringe 2B, is by the use of a highly absorbent material 40 having fast wicking rates, such as chemically modified cellulose fibers, contained within interior 26. Absorbent material 40 has the capability of expanding to many times its original volume when exposed to a fluid, thus being capable of filling interior 26 of dumping reservoir 24. Such chemically modified cellulose fibers are described in U.S. Pat. No. 4,256,111, incorporated herein by reference in its entirety. Other anti-sloshing methods, such as the use of labyrinths, banks of capillary tubes, or a combination of various techniques, can also be used. Preventing sloshing sounds from fluid sloshing in reservoir 24 is important to mimic the operation of the type-A syringe.

Another unwanted auditory signal from type-B syringes may be the sound of fluid jets exiting restrictor plate 34. This may be countered by lining the interior 26 of dumping reservoir 24 with a sound absorbent layer. Another consideration in the design of dumping reservoir 24 arises from the fact that with operational syringe 2A, the total weight of the syringe is reduced as liquid in barrel 6 is delivered into the patient. This is in contrast with non-operational syringe 2B in which the total weight of syringe 2B is not reduced when plunger 8 is pushed. Also, the weight distribution of syringe 2A is different from the weight distribution of syringe 2B following delivery. One way to mask these differences would be to make dumping reservoir 24 substantially heavier, for example ten times heavier, than the weight of the liquid in injector 4. Another way is to make dumping reservoir 24 a different shape than that illustrated so that the reservoir extends along a greater length of fluid connector 12 than suggested in the drawings. However, since 10 cc's of common infusates only weigh about 10 grams (0.3 ounce), this problem of weight shift should not prove too noticeable.

In use, injector 4 is commonly a conventional syringe assembly which can be prefilled, for example, with a pharmaceutical fluid agent or other infusate 3, or filled by the physician with the liquid infusate 3. While an infusate 3 in the form of a pharmaceutical fluid agent can be used for both type-A and type-B syringes, a less expensive placebo infusate 3 of the same appearance and viscosity, such as, for example, normal saline solution plus a colorant, could be provided for use with nonoperational syringe 20. Valve 18 is then turned to the purging position of FIGS. 3B and 6B by the manipulation of valve handle 22 as shown in the positions of FIGS. 3A and 6A. Once all excess air has been purged through discharge port 14, valve 18 is placed in the intermediate position (FIGS. 4B, 7B) and catheter fitting 15 is secured to the catheter. Valve 18 is then returned to the purge position and plunger 8 is actuated to purge the catheter. Valve handle 22 is then manipulated to turn valve 18 to the infusion position of FIG. 5B for infusion syringe 2A and to the infusion position of FIG. 8B for infusion syringe 2B. In the case of infusion syringe 2A, infusate 3 is delivered from infusion syringe 2A at a predetermined infusion pressure in a conventional manner. In the case of nonoperational infusion syringe 2B, infusate 3 is directed by valve 18B into dumping reservoir 24, when the infusion syringe 2B is operated at the same predetermine infusion pressure in a conventional manner.

Both the type-A and type-B infusion syringes are externally indistinguishable from each other by the user or the patient. The only identification used is an encrypted serial number. The encrypted serial number is then used by the researchers conducting the double blind test to identify which patients were treated with the drug and which patients were not. Additionally, researchers may verify that tamper-evident seal 32 is intact before opening screw on cap 30 at the end of reservoir body 28, to check whether dumping reservoir 24 contains any fluid, and then double check against the information from the encrypted serial number.

Modification and variation can be made to the disclosed embodiment without departing from the subject of the invention as defined in the following claims. For example, valve 18 could be something other than a rotary valve and could be configured differently from the example disclosed. Two types of dumping reservoirs 24 could be used; the operational dumping reservoir 24 shown in FIG. 9 could be used for the nonoperational, type-B infusion syringe 2B, while a nonoperational or dummy dumping reservoir could be used for operational syringe 2A since no liquid ever flows into it; externally, of course, the dumping reservoirs must appear identical. While a syringe-type injector 4 has been disclosed, other types of substance injectors for dispensing infusate 3, such as a bellows-type arrangement, could be used so that the infusion device could be something other than an infusion syringe. In some cases, discharge port 14 may not be connected directly or indirectly to a catheter but instead to a hypodermic needle or other tubular delivery device for intravenous or intramuscular fluid delivery. Dumping reservoir 24 could include an expandable pouch or other container which would provide at least a portion of the desired hydraulic back pressure and also work as an anti-sloshing element with or without an absorbent material 40 within the expandable pouch or other container.

What is claimed is:

1. A combination of A-type and B-type infusion devices, for use in double-blind clinical studies wherein an infusate is directed into a patient, comprising:

each of said type-A and type-B infusion devices comprising:
        a substance injector having an exit port; and
        a fluid connector having a discharge port defining a fluid path fluidly coupling the exit port with a discharge port;
    said type-A device comprising a type-A valve assembly located along the fluid connector, said type-A valve assembly comprising a type-A valve having a first port coupled to the exit port by the fluid connector, a second port, a third port coupled to the discharged port by the fluid connector, and a moveable element positionable between purge and infusion positions, said moveable element forming first and second fluid passageways between the first and third ports when in purge and infusion positions, to fluidly couple the exit and discharge ports through the first and third ports of the valve;
    said type-B device comprising a dumping reservoir and a type-B valve assembly located along the fluid connector, said type-B valve assembly comprising a type-B valve having a first port coupled to the exit port by the fluid connector, a second port coupled to the dumping reservoir, a third port coupled to the discharge port by the fluid connector, and a moveable element positionable between purge and infusion positions, wherein:
        the moveable element forms a purging fluid passageway between the first and third ports when in the purge position so to fluidly couple the exit and discharge ports through the first and third ports, and wherein
        the moveable element forms a dumping fluid passageway between the first and second ports when in the infusion position so to fluidly couple the exit port with the dumping reservoir through first and second ports, the first and third ports being fluidly isolated from one another when said B-type valve is in the infusion position;
    said type-A valve assembly further comprising a dumping reservoir coupled to the second port but fluidly isolated from said exit port when said type-A valve is in the infusion and purge positions; and
    said type-A and type-B infusion devices being externally effectively indistinguishable from each other.

2. The combination according to claim 1 wherein said substance injector comprises a barrel and a movable plunger movably mounted within the barrel.

3. The combination according to claim 1 wherein the fluid connector has a catheter fitting at the discharge port.

4. The combination according to claim 1 wherein the fluid connector has a hypodermic needle fitting at the discharge port.

5. The combination according to claim 1 wherein the type-A valve includes an intermediate position at which the exit port and the dumping reservoir are sealed.

6. The combination according to claim 1 wherein the dumping reservoir includes an anti-sloshing element to keep any infusate from sloshing around in the dumping reservoir.

7. The combination according to claim 6 wherein the anti-sloshing element is an absorbent anti-sloshing element.

8. The combination according to claim 1 wherein the dumping reservoir includes an air vent to provide relief for air being displaced by the fluid in the dumping reservoir.

9. The combination according to claim 1 further comprising means for restricting infusate flow into the dumping reservoir.

10. The combination according to claim 9 wherein the infusate flow restricting means is configured to mimic the infusate flow resistance created by infusate flowing from the type-A infusion device through a catheter.

11. The combination according to claim 1 wherein each said type-A and type-B device further comprises a pressure gauge fluidly coupled to the fluid path at a point between said exit port and said type-A and type-B valves, respectively.

12. The combination according to claim 1 wherein the dumping reservoir further comprises a reservoir body, an access member mounted to the reservoir body and a tamper-proof seal to indicate if the access member has been removed from the reservoir body.

13. The combination according to claim 1 wherein the type-A and type-B infusion devices are each marked with an encrypted serial number.

14. A method for directing an infusate into patients during a double-blind clinical study comprising the following step:

selecting type-A and type-B infusion devices, said type-A and type-B infusion devices comprising injectors containing fluid substances and dumping reservoirs, said type-A and said type-B infusion devices being externally effectively indistinguishable from one another;
    placing said type-A and type-B infusion devices in infusion positions;
    injecting said fluid substance from the type-A infusion device into a first patient;
    using said type-B infusion device in the same manner as said type-A infusion device while said type-B infusion device:

automatically diverts said fluid substance from said type-B infusion device into said dumping reservoir of said type-B infusion device; and mimics the operation of the type-A infusion device;

whereby there are no perceptible differences between the type-A and type-B infusion devices during use.

15. The method according to claim 14 further comprising the steps of:

placing said type-A and type-B infusion devices in purge positions; and purging said type-A and type-B infusion devices of air.

16. The method according to claim 15 further comprising the step of connecting discharge port fittings of the type-A and type-B infusion devices to tubular delivery devices following said purging steps.

17. The method according to claim 16 wherein the connecting step includes the step of selecting tubular delivery devices from the group of catheters and needle cannulas.

18. The method according to claim 16 further comprising the step of purging air from the tubular delivery device following the connecting step.

* * * * *